United States Patent [19]

Böhner et al.

[11] 4,422,867
[45] Dec. 27, 1983

[54] HERBICIDALLY ACTIVE UNSATURATED ESTERS OF HALOGENATED α-[4-(PYRIDYL-2'-OXY)-PHENOXY]-PROPIONIC ACIDS

[75] Inventors: Beat Böhner; Hermann Rempfler; Rolf Schurter, all of Binningen, Switzerland

[73] Assignee: Ciba-Geigy Corporation, Ardsley, N.Y.

[21] Appl. No.: 279,505

[22] Filed: Jul. 2, 1981

Related U.S. Application Data

[62] Division of Ser. No. 2,923, Jan. 12, 1979, Pat. No. 4,300,944.

[51] Int. Cl.³ .................. A01N 43/40; C07D 213/36
[52] U.S. Cl. ..................................... 71/094; 546/300; 546/302
[58] Field of Search .................. 71/94, 90, 88, 92; 546/300, 302

[56] References Cited

U.S. PATENT DOCUMENTS

| | | | |
|---|---|---|---|
| 4,003,734 | 1/1977 | Johnston | 71/94 |
| 4,169,720 | 10/1979 | Schacht et al. | 71/94 |
| 4,175,947 | 11/1979 | Koch et al. | 71/94 |
| 4,235,621 | 11/1980 | Mishyama et al. | 71/94 |
| 4,253,866 | 3/1981 | Schurter et al. | 71/94 |
| 4,325,729 | 4/1982 | Rempfler et al. | 546/300 |

*Primary Examiner*—Nicholas S. Rizzo
*Attorney, Agent, or Firm*—Frederick H. Rabin

[57] ABSTRACT

A class of herbicidal unsaturated esters of α-[4-(3',5'-dihalogeno-pyridyl-2'-oxy)-phenoxy]-propionic and -thiolpropionic acid of the formula

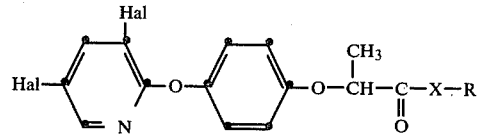

wherein Hal is chlorine or bromine, X is oxygen or sulfur, and R is an unsubstituted or halogenated aliphatic or alicyclic radical which may contain nitrogen, and which posseses at least one double and/or triple bond, with the proviso that if X is oxygen, R is not an unsubstituted alkenyl radical. These new esters are useful for selective post-emergent control of grassy weeds in cultivated plants such as wheat, barley, rice and soybean.

6 Claims, No Drawings

HERBICIDALLY ACTIVE UNSATURATED ESTERS OF HALOGENATED α-[4-(PYRIDYL-2'-OXY)-PHENOXY]-PROPIONIC ACIDS

This is a division of application Ser. No. 002,923 filed on Jan. 12, 1979, now U.S. Pat. No. 4,300,944.

The present invention relates to novel herbicidally active unsaturated esters of α-[4-(3',5'-dihalogenopyridyl-2'-oxy)-phenoxy]-propionic acids and -thiopropionic acids, to processes for their preparation, to herbicidal agents which contain these novel compounds as active ingredients, and to the use of the novel active substances, and of compositions which contain them, for selectively controlling weeds in cultivated plant crops.

In recent years, numerous derivatives of parasubstituted hydroxy-diphenyl ethers have been disclosed, compare German Offenlegungsschriften Nos. 2,223,894, 2,433,067, 2,531,643, 2,649,706, 2,609,461, 2,611,695, 2,623,558, 2,628,384, 2,652,384, 2,730,591 and 2,809,541.

Furthermore, heterocyclic analogs, for example correspondingly substituted pyridyl phenyl ethers, have been disclosed, compare German Offenlegungsschrift No. 2,546,251, Japanese Pat. No. 1,139,627 and German Offenlegungsschrift No. 2,732,846.

We have now found, surprisingly, that the novel active substances according to the present invention are superior to the commercially available products and to the structurally most closely related compounds in the patent literature in respect of selectively controlling weeds.

The novel unsaturated α-[4-(3',5'-dihalogenopyridyl-2'-oxy)-phenoxy]-propionic acid esters and -thiopropionic acid esters of the present invention have the formula I

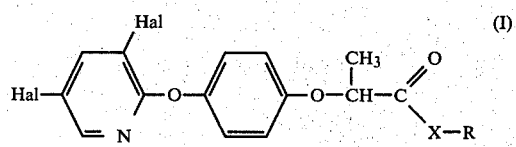

wherein Hal is chlorine or bromine, and the meaning of one Hal is independent of the meaning of the other, X is an oxygen or sulfur atom and R is an unsubstituted or halogenated aliphatic or alicyclic radical, which may contain nitrogen, and possesses at least one double bond and/or triple bond, with the proviso that if X is oxygen, R is not an unsubstituted alkenyl radical.

In the above definition, aliphatic and alicyclic radicals possessing a double and/or triple bond are not only unsubstituted or substituted (for example halogenated) alkenyl and alkynyl radicals, but also radicals which contain a nitrogen atom bonded to an adjacent carbon atom by a double or triple bond, for example the cyano group —C≡N or one of the groups

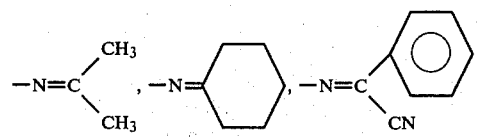

and the like. Accordingly, a cyanoalkyl group present as an ester radical also falls under the above definition.

The unsaturated aliphatic ester radicals R may be straight-chain or branched and the double or triple bond may be in the terminal position or in the interior of the —C—C— or —C—N— chain. The alkenyl and alkynyl radicals may also be substituted, in particular by halogen, for example chlorine or bromine.

In formula I, Hal is preferably chlorine. Amongst the radicals R, those with a triple bond (—C≡C—) are to be preferred, in respect of their action, to those possessing only double bonds, whilst the action of the latter is, in turn, somewhat superior to that of the cyanoalkyl esters and oxime esters.

The active substances according to the invention, of the formula I, and the herbicidal agents in which they are present as active ingredients, may in particular be used for selectively controlling grass-like weeds, which are difficult to control, in cultivated plant crops, including monocotyledonous cultivated plants, for example wheat and other varieties of cereals. Accordingly, the compounds of the invention are well tolerated by cultivated plants such as wheat, and are very effective against grass-like weeds.

The previously known 2,4-dichlorophenoxy-phenoxy derivatives of the prior art, such as the saturated compounds, and the unsaturated compounds containing double or triple bonds, of German Offenlegungsschriften Nos. 2,223,894, 2,623,558, 2,628,384 and 2,611,695, referred to above, are not entirely satisfactory in respect of their activity against grass-like weeds which are difficult to control, especially when the compounds are used in small amounts.

The previously known substituted pyridyloxy-phenoxyalkanecarboxylic acid derivatives of the prior art, for example the esters and thioesters described in German Offenlegungsschrift No. 2,546,251, and nitriles and esters with other substituents in the pyridyloxy radical, are either too aggressive towards sensitive cultivated plants, for example wheat, or, if they are well tolerated, are insufficiently active against the grass-like weeds to be controlled.

Surprisingly, the active substances according to the invention are distinguished, compared to the known saturated esters and thiol-esters of the pyridyloxy-α-phenoxy-propionic acid series, by distinctly better toleration by cultivated plants, especially wheat, barley and rice (that is to say by better selectivity), whilst they are distinguished compared to known aromatic unsaturated esters and thiol-esters by being more active against grass-like weeds, especially *Avena fatua* (species of wild oats).

Accordingly, it was the object of the present invention to provide novel esters from the series of the halogenated 4-(pyridyloxy)-α-phenoxy-propionic acids and thiopropionic acids, which are superior to known compounds of similar structure in respect of their herbicidal action against grass-like weeds which are difficult to control, and are better tolerated by important cultivated plants such as wheat, barley and rice, and thus represent an enrichment of the art.

The novel esters of the formula I may be prepared by methods known per se.

According to one of these methods, a corresponding α-[4-(3',5'-dihalogeno-pyridyl-2'-oxy)-phenoxy]-propionic acid halide of the formula II

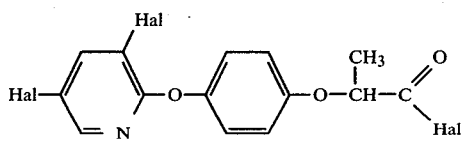

wherein each "Hal" is a halogen atom, is reacted with an alcohol or thiol of the formula III

wherein R and X are as defined in formula I, in the presence of a basic acid acceptor.

According to another method, the corresponding hydroxy-phenyl pyridyl ether, or a salt thereof, of the formula IV

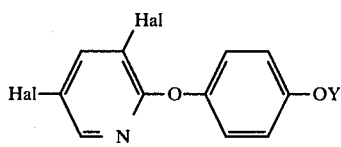

wherein Y is hydrogen or one equivalent of an alkali metal cation or alkaline earth metal cation is reacted with an α-halogenopropionic acid ester or α-halogeno-thiopropionic acid ester of the formula V

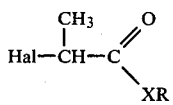

in the presence of an acid-binding agent (a base).

The reactions are preferably carried out in a solvent which is inert towards the reactants. A great variety of categories of compounds are suitable solvents, such as aliphatic and aromatic hydrocarbons and chlorohydrocarbons, for example ethylene chloride and the like, and polar organic solvents, such as alcohols, ethers, ketones, amides and stable esters, for example methyl ethyl ketone, dimethoxyethane, dimethyl formamide, dimethyl sulfoxide, tetrahydrofuran and the like.

Basic acid acceptors which may be used for the reaction with the halogen compounds of the formula II and V are aqueous alkali metal hydroxides, such as KOH and NaOH, and other conventional basic compounds, such as carbonates ($K_2CO_3$, $NaHCO_3$) and alcoholates ($NaOCH_3$ and potassium tert.-butylate), but also organic bases, such as triethylamine and the like.

A number of the starting materials of the formulae II to V are known. Starting materials of these formulae which have not yet been described can be prepared in accordance with known processes.

The propionic acid esters and thiopropionic acid esters of the formula I (X=O or S) can also be obtained by reacting the corresponding free α-[4-(3',5'-dihalogenopyridyl-2'-oxy)-phenoxy]-propionic acid or -thiopropionic acid, or a metal salt of such an acid, with an unsaturated halide of the formula Hal-R in the presence of a base.

The free thiopropionic acid and its metal salts, which may be used for this purpose, and their preparation from the corresponding propionic acid halide by reaction with hydrogen sulfide, $Na_2S$ or NaHS in the presence of a basic acid acceptor form the subject of a pending patent application. α-[4-(3',5'-Dichloropyridyl-2'-oxy)-phenoxy]-thiopropionic acid prepared by this method is an oil with a refractive index $n_D^{21}=1.5787$, which melts at 85°–87° C. after crystallisation.

Finally, unsaturated esters of α-[4-(3',5'-dihalogeno-pyridyl-2'-oxy)-phenoxy]-propionic acid (X=oxygen) may also be prepared by esterifying the free acid directly with a corresponding alcohol in accordance with conventional methods.

The examples which follow illustrate the preparation of some active substances according to the invention, of the formula I. Other end products of the formula I, which have been prepared correspondingly or by one of the other methods mentioned in the text are tabulated after the examples.

EXAMPLE 1

10.2 g (0.04 mol) of 4-(3',5'-dichloro-pyridyl-2'-oxy)-phenol, 8.4 g (0.044 mol) of propargyl α-bromopropionate and 8.5 g (0.06 mol) of potassium carbonate in 120 ml of methyl ethyl ketone are refluxed for 6 hours. The salts are filtered off and the filtrate is evaporated. The product is purified by dissolving it in chloroform and filtering the solution through a short silica gel column. After evaporating off the chloroform, 9 g (62%) of propargyl α-[4-(3',5'-dichloro-pyridyl-2'-oxy)-phenoxy]-propionate are obtained as a pale yellow oil with a refractive index of $n_D^{40}=1.5524$.

EXAMPLE 2

30 ml of thionyl chloride are added to 26.8 g (0.082 mol) of α-[4-(3',5'-dichloro-pyridyl-2'-oxy)-phenoxy]-propionic acid and when the evolution of gas has subsided the mixture is heated to 50° C. After 2 hours, the reaction mixture is evaporated in vacuo, 100 ml of toluene are added to the residue and the solvent is again evaporated. The product obtained is a dark brown oil which slowly starts to crystallize. This affords 25.9 g (86.7%) of α-[4-(3',5'-dichloro-pyridyl-2'-oxy)phenoxy]-propionic acid chloride with a melting point of 45° C.

17.3 g (0.05 mol) of this acid chloride are added dropwise to a mixture of 4.6 g (0.055 mol) of 70% strength aqueous glycollic acid nitrile, 7.6 g (0.055 mol) of triethylamine and 100 ml of methylene chloride, during which addition the temperature rises to 35° C. After one hour, 100 ml of water are added to the reaction mixture. The organic phase is filtered through a small silica gel column and on evaporating the filtrate 14.7 g (80.3%) of cyanomethyl α-[4-(3',5'-dichloro-pyridyl-2'-oxy)-phenoxy]propionate are obtained in the form of white crystals with a melting point of 67°–68° C.

EXAMPLE 3

17.2 g (0.0496 mol) of α-[4-(3',5'-dichloropyridyl-2'-oxy)-phenoxy]-propionic acid chloride, prepared as described in Example 2, are added dropwise to a mixture of 8.9 g of KOH in 4.9 ml of water and 75 ml of dimethoxyethane which has been saturated with $H_2S$, the saturation being effected with vigorous stirring at 10°–15° C. During the dropwise addition, the temperature of the reaction mixture is kept at 10° C. by means of an ice bath. The reaction mixture is then stirred for 30 minutes at room temperature, after which it is poured onto 150 ml of ice/water. The turbid brown solution is brought to pH 1 with concentrated HCl. This causes a brown oil to precipitate, which is taken up in methylene chloride. The organic phase is directly charged onto a small silica gel column, which is eluted with methylene chloride. After evaporating the pale yellow solution, a clear orange oil is obtained. This crystallises when triturated with petroleum ether, affording 16.8 g of α-[4-(3′,5′-dichloro-pyridyl-2′-oxy)-phenoxy]-thiopropionic acid as yellow crystals with a melting point of 85°–87° C.

10.0 g (0.029 mol) of this thiopropionic acid are dissolved in 50 ml of methyl ethyl ketone and 4.5 g (0.033 mol) of potassium carbonate are added at room temperature. This brings about an exothermic reaction accompanied by slight evolution of gas, with the temperature rising to 30° C. When the reaction has subsided, 3.0 g (0.033 mol) of 2-methallyl chloride are added at 27° C., whereupon the temperature rises to 40° C. The yellow suspension turns white. After 15 minutes, the reaction mixture is filtered through a small silica gel column, which is then washed with methyl ethyl ketone. Evaporating the yellow solution under a waterpump vacuum affords 9.7 g (83.6%) of S-2-methallyl α-[4-(3′,5′-dichloro-pyridyl-2′-oxy)-phenoxy]-thiopropionate as a yellow clear oil with a refractive index of $n_D^{20} = 1.5796$.

EXAMPLE 4

17.2 g (0.05 mol) of α-[4-(3′,5′-dichloro-pyridyl-2′-oxy)-phenoxy]-propionic acid chloride, prepared as described in Example 2, are dissolved in 20 ml of methylene chloride and the solution is added dropwise, at 20° C., to a mixture of 4.0 g (0.055 mol) of acetone-oxime, 7.3 ml of 30% strength NaOH solution, 30 ml of water and 50 ml of methylene chloride. The mixture is then stirred for a further hour, after which the organic phase is separated off. The latter is charged directly onto a small silica gel column, and the product is eluted with methylene chloride. The colourless clear solution is evaporated under a waterpump vacuum, affording 8.4 g (44.0%) of α-[4-(3′,5′-dichloro-pyridyl-2′-oxy)-phenoxy]-propionic acid acetone-oxime ester as a clear, yellowish oil with a refractive index of $n_D^{20} = 1.5678$.

EXAMPLE 5

16.4 g (0.05 mol) of α-[4-(3′,5′-dichloro-pyridyl-2′-oxy)-phenoxy]-propionic acid are dissolved in 500 ml of acetone and 7.6 g (0.055 mol) of potassium carbonate are added. This suspension is stirred for 1 hour at 45° C. 6.8 ml (0.075 mol) of 1,3-dichloropropene and 0.5 g of potassium iodide are then added. The reaction mixture is then stirred for 3 hours at 55° C., after which no starting material is left. The suspension is cooled to room temperature and filtered through a small silica gel column. Evaporation affords 18.2 g (90.6%) of a yellow clear oil, which is 3-chloroallyl α-[4-(3′,5′-dichloro-pyridyl-2′-oxy)-phenoxy]-propionate, of refractive index $n_D^{25} = 1.5553$, and having the formula

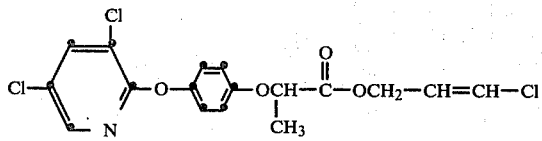

EXAMPLE 6

328 g (1 mol) of α-[4-(3′,5′-dichloro-pyridyl-2′-oxy)-phenoxy]-propionic acid, 84 g (1.5 mols) of propargyl alcohol and 5 g of p-toluenesulfonic acid in toluene are refluxed for 14 hours under a water separator. The solution in the reaction vessel is evaporated, the residue is taken up in ether and this mixture is clarified by filtration. The p-toluenesulfonic acid is removed by shaking with aqueous bicarbonate solution. After drying the organic phase with magnesium sulfate, the ether is evaporated. 355 g (96.9% of theory) of pure propargyl ester of the starting acid are obtained as an oil which crystallises slowly. These crystals have a melting point of 62°–65° C.

The compounds described in the preceding examples, and further compounds of the formula I, prepared analogously, are tabulated below.

(1) α-[4-(3′,5′-Dichloro-pyridyl-2′-oxy)-phenoxy]-propionic acid and -thiopropionic acid esters of the formula

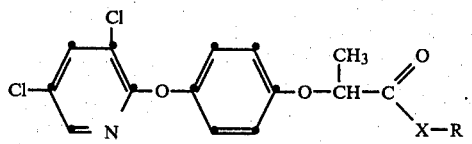

| | (a) Alkynyl derivatives | | | |
|---|---|---|---|---|
| Com- | | | Physical data | |
| pound No. | X | R | $n_D$ | M.p. °C. |
| 1 | O | —CH₂—C≡CH | $n^{40} = 1.5524$ | 62–65° |
| 2 | S | —CH₂—C≡CH | $n^{21} = 1.5988$ | 89–91° |
| 3 | S | —CH₂—C≡C—CH₂—Cl | $n^{25} = 1.5945$ | |
| 4 | S | —CH₂—C≡C—CH₂—Cl | $n^{25} = 1.5581$ | |
| 5 | O | —C(CH₃)₂—C≡CH | $n^{25} = 1.5561$ | |
| 6 | O | —CH₂—CH=C(CH₃)—C≡CH (trans) | $n^{25} = 1.5588$ | |
| 7 | O | —CH₂—CH=C(CH₃)—C≡CH (cis) | $n^{25} = 1.5440$ | |
| 8 | O | cyclohexyl with H and C≡CH | | 90–92° |
| 9 | O | —CH(C₃H₇(n))—C≡CH | $n^{30} = 1.5488$ | |
| 10 | O | —C(CH₃)(CH=CH₂)—C≡CH | $n^{30} = 1.5559$ | |
| 11 | O | —C(CH₃)(C₂H₅)—C≡CH | $n^{30} = 1.5523$ | |
| 12 | O | —CH(C₂H₅)—C≡CH | | |

-continued

(a) Alkynyl derivatives

| Compound No. | X | R | Physical data $n_D$ | M.p. °C. |
|---|---|---|---|---|
| 13 | O | —CH$_2$—CH=C(—CH$_3$)—C≡CH | | |
| 14 | O | —C(CH$_3$)(C$_3$H$_7$(iso))—C≡CH | | |
| 15 | O | —C(C$_2$H$_5$)(C$_2$H$_5$)—C≡CH | | |
| 16 | O | —C(C$_3$H$_7$(iso))(C$_3$H$_7$(iso))—C≡CH | | |
| 17 | O | —C(CH$_3$)(C$_3$H$_7$(n))—C≡CH | | |
| 18 | O | —C(C$_3$H$_7$(n))(C$_3$H$_7$(n))—C≡CH | | |
| 19 | O | —CH(CH$_3$)—C≡CH | | |

(b) Alkenyl derivatives

| Compound No. | X | R | Physical data $n_D$ | M.p. °C. |
|---|---|---|---|---|
| 20 | S | —CH$_2$—CH=CH$_2$ | $n^{21}$ = 1.5854 | |
| 21 | S | —CH$_2$—C(CH$_3$)=CH$_2$ | $n^{20}$ = 1.5796 | |
| 22 | S | —CH$_2$—CH$_2$—CH=CH$_2$ | $n^{20}$ = 1.5878 | |
| 23 | S | —CH$_2$—CH=CH—Cl | $n^{24}$ = 1.5795 | |
| 24 | S | —CH$_2$—C(Br)=CH$_2$ | $n^{24}$ = 1.5795 | |
| 25 | O | —CH$_2$—C(Br)=CH$_2$ | $n^{24}$ = 1.5722 | |
| 26 | S | —CH$_2$—CH=CH—CH$_3$ | $n^{25}$ = 1.5789 | |
| 27 | S | —CH$_2$—C(Cl)=CH—Cl | $n^{25}$ = 1.5779 | |
| 28 | S | —CH$_2$—C(Cl)=CH$_2$ | $n^{25}$ = 1.5913 | |
| 29 | S | —CH$_2$—CH=C(CH$_3$)(Cl) | $n^{25}$ = 1.5772 | |
| 30 | O | —CH$_2$—CH=CH—Cl | $n^{25}$ = 1.5553 | |
| 31 | O | —CH$_2$—C(Cl)=CH$_2$ | | |
| 32 | S | —CH$_2$—CH=CCl$_2$ | | |
| 33 | O | —CH$_2$—CH=CCl$_2$ | | |
| 34 | S | —CH$_2$—CH=C(CH$_3$)$_2$ | | |

(c) Cyanoalkyl derivatives

| Compound No. | X | R | Physical data $n_D$ | M.p. °C. |
|---|---|---|---|---|
| 35 | O | —CH$_2$—CN | | 67–68° |
| 36 | O | —CH(CH$_3$)—CN | $n^{20}$ = 1.5564 | |
| 37 | S | —CH$_2$—CN | | 85–88° |
| 38 | S | —CH$_2$—CH$_2$—CN | $n^{20}$ = 1.5806 | |
| 39 | S | —CH$_2$—CH$_2$—CH$_2$—CN | $n^{20}$ = 1.5630 | |
| 40 | O | —CH$_2$—CH$_2$—CN | | 98–100° |
| 41 | S | —CH(CH$_3$)—CN | $n^{25}$ = 1.5623 | |
| 42 | O | —CH(C$_2$H$_5$)—CN | $n^{25}$ = 1.5478 | |
| 43 | O | —C(CH$_3$)(CH$_3$)—CN | | 73–75° |
| 44 | S | —C(CH$_3$)(CH$_3$)—CN | | |
| 45 | O | —C(C$_2$H$_5$)(CH$_3$)—CN | | |
| 46 | O | —C(C$_2$H$_5$)(C$_2$H$_5$)—CN | | |
| 47 | S | —CH$_2$—CH(CH$_3$)—CN | | |
| 48 | O | —CH$_2$—CH(CH$_3$)—CN | | |

-continued

(c) Cyanoalkyl derivatives

| Compound No. | X | R | Physical data $n_D$ | M.p. °C. |
|---|---|---|---|---|
| 49 | S | ![cyclohexyl with H and CN] | | |
| 50 | O | ![cyclohexyl with H and CN] | | |

(d) Oxime derivatives

| Compound No. | X | R | Physical data $n_D$ | M.p. °C. |
|---|---|---|---|---|
| 51 | O | $-N=C(CH_3)_2$ | $n^{20} = 1.5678$ | |
| 52 | O | $-N=C$(H)(cyclohexyl) | $n^{25} = 1.5667$ | |
| 53 | O | $-N=C$(CN)(phenyl) | $n^{25} = 1.5539$ | 96–99° |

Further oxime esters:
(54) acetone-oxime ester
(55) 3,5,5-trimethyl-2-cyclohexenone-oxime ester
(56) acetophenone-oxime ester
(57) methyl isobutyl ketone-oxime ester
(58) benzaldoxime ester
(59) methyl ethyl ketone-oxime ester
(60) diethyl ketone-oxime ester
(61) methyl propyl ketone-oxime ester
(62) methyl tert.-butyl ketone-oxime ester
(63) di-isobutyl ketone-oxime ester
(64) cyclopentanone-oxime ester
(65) 2-chlorocyclohexanone-oxime ester
(66) 2-methylcyclohexanone-oxime ester
(67) 3-methylcyclopentanone-oxime ester.

(2) α-[4-(3',5'-Dibromo-pyridyl-2'-oxy)-phenoxy]propionic acid and -thiopropionic acid esters of the formula

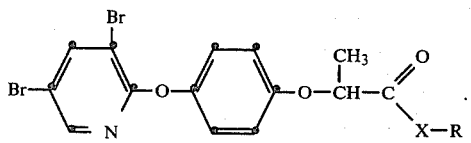

| Compound No. | X | R | Physical data $n_D$ | M.p. °C. |
|---|---|---|---|---|
| 68 | S | $-CH_2-C{\equiv}CH$ | $n^{25} = 1.6120$ | |
| 69 | S | $-CH_2-C(CH_3)=CH_2$ | $n^{25} = 1.5865$ | |
| 70 | O | $-CH_2-C{\equiv}CH$ | $n^{40} = 1.5672$ | |
| 71 | O | $-N=C(CH_3)_2$ | | |
| 72 | O | $-N=$(cyclohexyl-H) | | |
| 73 | O | $-CH_2-CN$ | | |
| 74 | O | $-C(CH_3)_2-CN$ | | |
| 75 | S | $-CH_2-CH=CH_2$ | | |

The invention also relates to herbicidal agents which contain a novel active ingredient of the formula I, and to processes for pre-emergent and more particularly post-emergent weed control, especially the control of monocotyledonous grass-like weeds.

The agents according to the invention may be in the form of the conventional formulations.

The agents according to the invention are prepared in a manner known per se by intimately mixing and grinding active substances of the formula I with suitable carriers, with or without the addition of dispersants or solvents which are inert towards the active substances. The active substances may be present, and can be used, as the following formulations:

Solid formulations: dusts, tracking powders, granules (coated granules, impregnated granules and homogeneous granules);
Active substance concentrates which are dispersible in water: wettable powders, pastes and emulsions;
Liquid formulations: solutions.

To prepare solid formulations (dusts, tracking powders and granules) the active substances are mixed with solid carriers. Examples of suitable carriers are kaolin, talc, bolus, loess, chalk, limestone, lime grits, attaclay, dolomite, diatomaceous earth, precipitated silica, alkaline earth metal silicates, sodium and potassium aluminosilicates (feldspars and mica), calcium and magnesium sulfates, magnesium oxide, ground plastics, fertilisers, such as ammonium sulfate, ammonium phosphate, ammonium nitrate and urea, ground vegetable products, such as cereal flour, bark powder, wood flour, nutshell flour, cellulose powder, residues from plant extractions, active charcoal and the like, these materials being used individually or as mixtures with one another.

Granules may be prepared by dissolving the active substances in an organic solvent, applying the resulting solution to a granulated material, for example attapulgite, SiO$_2$, granicalcium or bentonite, and then evaporating the organic solvent.

Polymer granules may be prepared by, for example, impregnating finished porous polymer granules, such as urea/formaldehyde polymers, polyacrylonitrile and polyesters, having a certain surface area and an advantageous predetermined absorption/desorption ratio, with the active substances, for example in the form of their solutions (in a low-boiling solvent) and removing the solvent. Such polymer granules, in the form of micro-granules with bulk densities of, preferably, 300 g/liter to 600 g/liter, may also be applied by means of atomisers. This atomising can be carried out over large areas to be treated, by using aircraft.

Granules may also be obtained by compacting the carrier together with the active substances and additives and then comminuting the mixture.

It is also possible to add to these agents adjuvants which stabilise the active substance, and/or non-ionic, anionic and cationic substances which, for example, improve the adhesion of the active substances to plants and to parts of plants (adhesives and glues) and/or which ensure better wettability (wetting agents) and dispersibiity (dispersants). Examples of suitable adhesives are an olein-chalk mixture, cellulose derivatives (methylcellulose and carboxymethylcellulose), hydroxyethylene glycol ethers of monoalkylphenols and dialkylphenols, with 5 to 15 ethylene oxide units per molecule and 8 to 9 carbon atoms in the alkyl radical, ligninsulfonic acid, its alkali metal salts and alkaline earth metal salts, polyethylene glycol ethers (carbowaxes), fatty alcohol polyglycol ethers with 5 to 20 ethylene oxide units per molecule and 8 to 18 carbon atoms in the fatty alcohol part, condensation products of ethylene oxide and propylene oxide, polyvinylpyrrolidones, polyvinyl alcohols, urea-formaldehyde condensation products and latex products.

Concentrates of active substances which are dispersible in water, i.e. wettable powders, pastes and emulsion concentrates, are agents which can be diluted with water to any desired concentration. They comprise the active substance and a carrier, with or without additives which stabilise the active substance, surfactants, antifoam agents and solvents.

The wettable powders and pastes are obtained by mixing the active substances with dispersants and pulverulent carriers, and grinding the mixture, in suitable equipment, until a homogeneous product is obtained. Suitable carriers are, for example, those mentioned above for solid formulations. In some cases it is advantageous to use mixtures of different carriers. Examples of dispersants which may be used are condensation products of sulfonated naphthalene, and sulfonated naphthalene derivatives, with formaldehyde, condensation products of naphthalene or of naphthalenesulfonic acids with phenol and formaldehyde, alkali metal salts, ammonium salts and alkaline earth metal salts of lignin-sulfonic acid, alkylarylsulfonates, alkali metal salts and alkaline earth metal salts of dibutylnaphthalenesulfonic acid, fatty alcohol sulfates, for example salts of sulfated hexadecanols and heptadecanols and salts of sulfated fatty alcohol polyethylene glycol ethers, the sodium salt of oleyl methyl tauride, di-tertiary acetylene glycols, dialkyldilaurylammonium chloride and alkali metal salts and alkaline earth metal salts of fatty acids.

Suitable anti-foam agents are, for example, silicones.

The active substances are mixed with the abovementioned additives, and the mixture is ground, sieved and screened, in such a way that in the case of wettable powders the solid component does not exceed a particle size of 0.02 to 0.04 mm and in the case of pastes it does not exceed 0.03 mm. To prepare emulsion concentrates and pastes, dispersants, such as those mentioned in the preceding paragraphs, organic solvents and water are used. Examples of suitable solvents are alcohols, xylenes, toluene, dimethyl sulfoxide, N,N-dialkylated amides and trialkylamines. The solvents must be virtually odourless, non-phytotoxic and inert towards the active substances, and must not be highly inflammable.

The agents according to the invention can also be used in the form of solutions. For this purpose, the active substance of the formula I, or several such substances, is or are dissolved in suitable organic solvents, solvent mixtures, water or mixtures of organic solvents with water. Organic solvents which may be used are aliphatic and aromatic hydrocarbons, their chlorinated derivatives and alkylnaphthalenes, these being employed individually or as mixtures with one another.

The content of active substance in the agents described above is between 0.1 and 95%, preferably between 1 and 80%. The formulations can be diluted down to 0.001%. The amounts used are as a rule 0.1 to 10 kg of active substance/hectare, preferably 0.25 to 5 kg of active substance/hectare. The active substances of the formula I can for example be formulated as follows (parts are by weight):

Wettable powders

The following constituents are used to prepare (a) a 50%, (b) a 25% and (c) a 10% wettable powder:

(a) 50 parts of propargyl α-[4-(3′,5′-dichloropyridyl-2′-oxy)-phenoxy]-propionate, 5 parts of sodium dibutylnaphthylsulfonate, 3 parts of a 3:1:1 naphthalenesulfonic acid/phenolsulfonic acid/formaldehyde condensate, 20 parts of kaolin, 22 parts of Champagne chalk;

(b) 25 parts of the above active substance, 5 parts of sodium oleyl methyl tauride, 2.5 parts of a naphthalenesufonic acid/formaldehyde condensate, 0.5 part of carboxymethylcellulose, 5 parts of neutral potassium aluminosilicate, 62 parts of kaolin;

(c) 10 parts of the above active substance, 3 parts of a mixture of the sodium salts of sulfated saturated fatty alcohols, 5 parts of a naphthalenesulfonic acid/formaldehyde condensate, 82 parts of kaolin.

The indicated active substance is applied to the corresponding carriers (kaolin and chalk) and the material is then mixed and ground, to yield wettable powders of excellent wettability and suspending power. By diluting such wettable powders with water, it is possible to obtain suspensions of any desired concentration of active substance. Such suspensions are used for controlling weeds and grass-like weeds in crops of cultivated plants by the post-emergent method.

Paste

The following substances are used to prepare a 45% paste:

45 parts of S-propargyl α-[4-(3′,5′-dichloropyridyl-2′-oxy)-phenoxy]-thiopropionate, 5 parts of sodium aluminosilicate, 14 parts of cetyl polyethylene glycol ether with 8 mols of ethylene oxide, 1 part of oleyl polyethylene glycol ether with 5 mols of ethylene oxide, 2 parts of spindle oil, 23 parts of water, 10 parts of polyethylene oxide.

The active substance is homogeneously mixed with the adjuvants in appropriate equipment and the mixture is ground, yielding a paste from which, by dilution with water, it is possible to obtain suspensions of any desired concentration.

Emulsion concentrate

The following ingredients are mixed to prepare a 25% emulsion concentrate:

25 parts of S-2-methallyl α-[4(3',5'-dichloropyridyl-2'-oxy)-phenoxy]-thiopropionate, 10 parts of a mixture of polyoxyethyleneated nonylphenol and calcium dodecylbenzenesulfonate, 10 parts of cyclohexanone, 55 parts of xylene. This concentrate can be diluted with water to give emulsions of the concentrations suitable for application.

Instead of using the particular active substances indicated in the preceding formulation examples, it is also possible to use any other of the compounds comprised by the Formula I.

Agents according to the invention which contain, as the active ingredient, at least one compound of the formula I, are particularly suitable for the selective control of monocotyledonous grass-like weeds which are difficult to control, for example *Avena fatua* (wild oats), Rotboellia, Digitaria, Setaria and the like, when used by the pre-emergent method and especially by the post-emergent method in cultivated plant crops, for example wheat, barley and rice, but also soybean, cotton, sugar cane and the like.

Pre-emergent herbicidal action (germination inhibition)

In a greenhouse, immediately after sowing the test plants in seed dishes, the surface of the soil is treated with an aqueous dispersion of the active substances, obtained from a 25% emulsion concentrate or from a 25% wettable powder, the latter in the case of active substances which, because of insufficient solubility, cannot be prepared in the form of an emulsion concentrate. Four different concentration series were used, corresponding to 4, 2, 1 and 0.5 kg of active substance per hectare. The seed dishes are kept in a greenhouse at 22°–25° C. and 50–70% relative atmospheric humidity; the experiment is evaluated after 3 weeks and the results are rated in accordance with the following scale of figures of merit:

1 = plants have not germinated or are totally withered
2–3 = very strong action
4–6 = medium action
7–8 = slight action
9 = no action (like untreated control).

The following were used as test plants:

| | |
|---|---|
| Hordeum (barley) | Setaria italica |
| Triticum (wheat) | Echinochloa crus galli |
| Zea (maize) | Beta vulgaris |
| Sorghum hybr. (millet) | Sida spinosa |
| Oryza (rice) | Sesbania exaltata |
| Glycine (soybean) | Amaranthus retroflexus |
| Gossypium (cotton) | Sinapis alba |
| Avena fatua | Ipomoea purpurea |
| Lolium perenne | Galium aparine |
| Alopecurus myosuroides | Pastinaca sativa |
| Bromus tectorum | Rumex sp. |
| Cyperus esculentus | Chrysanthemum leucum. |
| Rottboellia exaltata | Abutilon sp. |
| Digitaria sanguinalis | Solanum nigrum. |

Post-emergent herbicidal action (contact herbicide)

One or more weeds and cultivated plants, including both monocotyledonous and dicotyledonous species, were sprayed after emergence (in the 4-leaf to 6-leaf stage) with an aqueous active substance dispersion at various dosages (0.125, 0.25, 0.5 and 1 kg of active substance per hectare), the spray being applied to the plants, after which the latter were kept at 23°–26° C. and 45–60% relative atmospheric humidity. 15 days after treatment, the experiment is evaluated, the result being rated on the same scale of figures of merit as in the pre-emergent experiment.

In these post-emergent experiments (contact herbicide action) the structurally most closely related compounds from amongst the following previously known saturated and unsaturated hydroxy-diphenyl ether derivatives were in each case included in the test as comparison compounds.

| Compound | Formula | Literature |
|---|---|---|
| A | Cl-phenyl(Cl)-O-phenyl-O-CH(CH₃)-COOCH₃ | German Offenlegungsschrift 2,223,894 (No. 86) |
| B | Cl-pyridyl(Cl,N)-O-phenyl-O-CH(CH₃)-COOCH₃ | German Offenlegungsschrift 2,546,251 (No. 24) |
| C | Cl-phenyl(Cl)-O-phenyl-O-CH(CH₃)-COO-CH₂-C≡CH | German Offenlegungsschrift 2,623,558 (No. 36) |
| D | Cl-phenyl(Cl)-O-phenyl-O-CH(CH₃)-COS-CH₂-CH=CH₂ | German Offenlegungsschrift 2,623,558 (No. 90) |

| Compound | Formula | Literature |
|---|---|---|
| E | 4-Cl-pyridin-2-yl—O—C₆H₄—O—CH(CH₃)—COO—CH₂—CH=CH₂ | German Offenlegungsschrift 2,546,251 (No. 12) |
| F | 2,4-diCl-C₆H₃—O—C₆H₄—O—CH(CH₃)—COO—(CH₂)₂—C≡N | German Offenlegungsschrift 2,628,384 (No. 64) |
| G | 2,4-diCl-C₆H₃—O—C₆H₄—O—CH(CH₃)—COO—CH(CH₃)—C≡N | German Offenlegungsschrift 2,628,384 (No. 68) |
| H | 2,4-diCl-C₆H₃—O—C₆H₄—O—CH(CH₃)—CH₂—O—CH₂—C≡CH | German Offenlegungsschrift 2,611,695 (No. 140) |
| I | 2,4-diCl-C₆H₃—O—C₆H₄—O—CH(CH₃)—CH₂—O—CH₂—CH=CH₂ | German Offenlegungsschrift 2,611,695 (No. 139) |
| K | 3-Cl-4-(2,4-diCl)pyridin-2-yl—O—C₆H₄—O—CH(CH₃)—COO—CH₂—CH=CH₂ | German Offenlegungsschrift 2,546,251 (No. 31) |

First series of experiments

Cultivated plant: wheat (Triticum), "Probus" variety
Weed: wild oats (*Avena fatua*)
Amounts used: 1 kg and 0.5 kg of active substance per hectare.

| Compound No. | Wheat 1 kg | Wheat 0.5 kg | *Avena fatua* 1 kg | *Avena fatua* 0.5 kg |
|---|---|---|---|---|
| 1 | 4 | 9 | 1 | 1 |
| 2 | 2 | 8 | 1 | 1 |
| 3 | 9 | 9 | 1 | 2 |
| 4 | 9 | 9 | 1 | 1 |
| 5 | 5 | 9 | 1 | 1 |
| 6 | 5 | 9 | 1 | 1 |
| 7 | 6 | 7 | 1 | 1 |
| 8 | 9 | 9 | 1 | 2 |
| 9 | 4 | 9 | 1 | 1 |
| 10 | 9 | 9 | 1 | 1 |
| 11 | 9 | 9 | 1 | 1 |
| C | 9 | 9 | 4 | 7 |
| A | 9 | 9 | 3 | 5 |
| B | 2 | 3 | 1 | 1 |
| H | 9 | 9 | 9 | 9 |
| 20 | 7 | 9 | 1 | 2 |
| 21 | 3 | 9 | 1 | 1 |
| 22 | 7 | 9 | 1 | 1 |
| 23 | 4 | 9 | 1 | 1 |
| 24 | 7 | 9 | 1 | 2 |
| 25 | 5 | 8 | 1 | 1 |
| 26 | 8 | 9 | 1 | 1 |
| 27 | 9 | 9 | 1 | 1 |
| 28 | 8 | 9 | 1 | 1 |
| 29 | 6 | 9 | 1 | 2 |
| 30 | 4 | 8 | 1 | 1 |
| D | 9 | 9 | 3 | 8 |
| I | 9 | 9 | 9 | 9 |
| E | 4 | 5 | 2 | 4 |
| 35 | 2 | 5 | 1 | 1 |
| 36 | 3 | 9 | 1 | 1 |
| 37 | 4 | 9 | 1 | 1 |
| 38 | 7 | 9 | 1 | 2 |
| 39 | 7 | 9 | 1 | 2 |
| 40 | 9 | 9 | 1 | 4 |
| 41 | 8 | 9 | 1 | 1 |
| 42 | 3 | 9 | 1 | 1 |
| 51 | 6 | 9 | 1 | 1 |
| 52 | 8 | 9 | 1 | 1 |
| 53 | 5 | 9 | 1 | 1 |
| 68 | 4 | 9 | 1 | 1 |
| 69 | 7 | 9 | 1 | 2 |
| 70 | 3 | 5 | 1 | 1 |
| F | 9 | 9 | 4 | 9 |
| G | 9 | 9 | 5 | 7 |

Second series of experiments

Cultivated plant: barley (Hordeum), "Mazurka" variety
Weed: *Avena fatua* (wild oats)
Amount used: 0.25 kg of active substance per hectare.

| Compound No. | Barley | Avena fatua |
|---|---|---|
| 4 | 7 | 3 |
| 8 | 9 | 2 |
| 21 | 6 | 2 |
| 22 | 8 | 2 |
| 23 | 8 | 2 |
| 24 | 8 | 3 |
| 26 | 7 | 2 |
| 27 | 9 | 3 |
| 36 | 7 | 3 |
| 38 | 9 | 3 |
| 39 | 7 | 3 |
| 41 | 7 | 2 |
| 51 | 9 | 2 |
| 53 | 8 | 3 |
| 69 | 9 | 3 |
| A | 9 | 7 |
| C | 9 | 8 |
| D | 9 | 9 |
| K | 3 | 2 |

Third series of experiments
Cultivated plant: soybean, "Hark" variety
Weeds: millets (Rotboellia, Digitaria and Setaria)
Amounts used: 0.5, 0.25 and 0.125 kg of active substance per hectare.

| Cmpd. No | Soybean | | | Rotboellia | | | Digitaria | | | Setaria | | |
|---|---|---|---|---|---|---|---|---|---|---|---|---|
| | 0.5 | 0.25 | 0.125 | 0.5 | 0.25 | 0.125 | 0.5 | 0.25 | 0.125 | 0.5 | 0.25 | 0.125 |
| 1 | 9 | 9 | 9 | 1 | 1 | 1 | 1 | 1 | 1 | 1 | 1 | 1 |
| 2 | 9 | 9 | 9 | 1 | 1 | 1 | 1 | 1 | 1 | 1 | 1 | 1 |
| 3 | 9 | 9 | 9 | 2 | 6 | 8 | 2 | 2 | 5 | 1 | 3 | 4 |
| 4 | 9 | 9 | 9 | 1 | 1 | 3 | 1 | 1 | 2 | 1 | 1 | 1 |
| 5 | 9 | 9 | 9 | 1 | 1 | 3 | 1 | 1 | 1 | 1 | 1 | 1 |
| 6 | 9 | 9 | 9 | 1 | 1 | 2 | 1 | 1 | 1 | 1 | 1 | 1 |
| 7 | 9 | 9 | 9 | 1 | 1 | 2 | 1 | 1 | 1 | 1 | 1 | 1 |
| 8 | 9 | 9 | 9 | 1 | 8 | 8 | 1 | 1 | 3 | 1 | 1 | 2 |
| 9 | 9 | 9 | 9 | 1 | 1 | 2 | 1 | 1 | 1 | 1 | 1 | 1 |
| 10 | 9 | 9 | 9 | 1 | 1 | 1 | 1 | 1 | 1 | 1 | 1 | 1 |
| 11 | 9 | 9 | 9 | 1 | 1 | 1 | 1 | 1 | 1 | 1 | 1 | 1 |
| C | 9 | 9 | 9 | 2 | 3 | 5 | 4 | 5 | 6 | 1 | 1 | 3 |
| H | 9 | 9 | 9 | 9 | 9 | 9 | 9 | 9 | 9 | 9 | 9 | 9 |
| 20 | 9 | 9 | 9 | 1 | 1 | 2 | 1 | 1 | 1 | 1 | 1 | 1 |
| 21 | 9 | 9 | 9 | 1 | 1 | 1 | 1 | 1 | 1 | 1 | 1 | 1 |
| 22 | 9 | 9 | 9 | 1 | 1 | 3 | 1 | 1 | 1 | 1 | 1 | 1 |
| 23 | 9 | 9 | 9 | 1 | 1 | 2 | 1 | 1 | 1 | 1 | 1 | 1 |
| 24 | 9 | 9 | 9 | 1 | 1 | 2 | 1 | 1 | 1 | 1 | 1 | 1 |
| 25 | 9 | 9 | 9 | 1 | 1 | 1 | 1 | 1 | 1 | 1 | 1 | 1 |
| 26 | 9 | 9 | 9 | 1 | 1 | 2 | 1 | 1 | 1 | 1 | 1 | 1 |
| 27 | 9 | 9 | 9 | 1 | 2 | 6 | 1 | 1 | 1 | 1 | 1 | 1 |
| 28 | 9 | 9 | 9 | 1 | 1 | 2 | 1 | 1 | 2 | 1 | 1 | 1 |
| 29 | 9 | 9 | 9 | 1 | 1 | 3 | 1 | 2 | 2 | 1 | 1 | 1 |
| 30 | 9 | 9 | 9 | 1 | 1 | 2 | 1 | 2 | 2 | 1 | 1 | 1 |
| D | 9 | 9 | 9 | 2 | 3 | 8 | 2 | 6 | 6 | 1 | 4 | 4 |
| I | 9 | 9 | 9 | 9 | 9 | 9 | 9 | 9 | 9 | 9 | 9 | 9 |
| E | 9 | 9 | 9 | 2 | 3 | 5 | 2 | 2 | 3 | 1 | 2 | 4 |
| 35 | 9 | 9 | 9 | 1 | 1 | 1 | 1 | 1 | 1 | 1 | 1 | 1 |
| 36 | 9 | 9 | 9 | 1 | 1 | 1 | 1 | 1 | 1 | 1 | 1 | 1 |
| 37 | 9 | 9 | 9 | 1 | 1 | 2 | 1 | 1 | 1 | 1 | 1 | 1 |
| 38 | 9 | 9 | 9 | 1 | 2 | 5 | 1 | 1 | 1 | 1 | 1 | 1 |
| 39 | 9 | 9 | 9 | 1 | 3 | 6 | 1 | 1 | 1 | 1 | 1 | 2 |
| 40 | 9 | 9 | 9 | 1 | 3 | 5 | 1 | 1 | 2 | 1 | 1 | 5 |
| 41 | 9 | 9 | 9 | 1 | 1 | 2 | 1 | 1 | 2 | 1 | 1 | 1 |
| 42 | 9 | 9 | 9 | 1 | 1 | 3 | 1 | 1 | 1 | 1 | 1 | 1 |
| 51 | 9 | 9 | 9 | 1 | 1 | 2 | 1 | 1 | 1 | 1 | 1 | 1 |
| 52 | 9 | 9 | 9 | 1 | 1 | 2 | 1 | 1 | 2 | 1 | 1 | 1 |
| 53 | 9 | 9 | 9 | 1 | 1 | 3 | 1 | 1 | 2 | 1 | 1 | 1 |
| 68 | 9 | 9 | 9 | 1 | 2 | 6 | 1 | 2 | 2 | 1 | 1 | 2 |
| 69 | 9 | 9 | 9 | 3 | 3 | 7 | 1 | 1 | 2 | 1 | 1 | 2 |
| 70 | 9 | 9 | 9 | 1 | 1 | 2 | 1 | 1 | 2 | 1 | 1 | 2 |
| F | 9 | 9 | 9 | 5 | 7 | 9 | 6 | 7 | 8 | 2 | 4 | 7 |
| G | 9 | 9 | 9 | 4 | 7 | 9 | 4 | 7 | 8 | 2 | 3 | 7 |

Fourth series of experiments
Cultivated plant: dry rice "Caloro" variety
Weeds: Digitaria and Setaria
Amounts used: 0.5, 0.25 and 0.125 kg of active substance per hectare.

| Compound No. | Dry rice | | | Digitaria | | | Setaria | | |
|---|---|---|---|---|---|---|---|---|---|
| | 0.5 | 0.25 | 0.125 | 0.5 | 0.25 | 0.125 | 0.5 | 0.25 | 0.125 |
| 2 | 4 | 5 | 8 | 1 | 1 | 1 | 1 | 1 | 1 |
| 4 | 5 | 8 | 9 | 1 | 1 | 2 | 1 | 1 | 1 |
| 5 | 5 | 5 | 9 | 1 | 1 | 1 | 1 | 1 | 1 |
| 8 | 7 | 9 | 9 | 1 | 1 | 3 | 1 | 1 | 2 |
| 9 | 6 | 6 | 9 | 1 | 1 | 1 | 1 | 1 | 1 |
| 10 | 6 | 8 | 9 | 1 | 1 | 1 | 1 | 1 | 1 |
| 11 | 6 | 9 | 9 | 1 | 1 | 1 | 1 | 1 | 1 |
| C | 9 | 9 | 9 | 4 | 5 | 6 | 1 | 1 | 3 |
| H | 9 | 9 | 9 | 9 | 9 | 9 | 9 | 9 | 9 |
| 20 | 6 | 6 | 8 | 1 | 1 | 1 | 1 | 1 | 1 |
| 21 | 6 | 8 | 9 | 1 | 1 | 1 | 1 | 1 | 1 |
| 22 | 4 | 8 | 9 | 1 | 1 | 1 | 1 | 1 | 1 |
| 23 | 8 | 8 | 9 | 1 | 1 | 1 | 1 | 1 | 1 |
| 24 | 5 | 8 | 9 | 1 | 1 | 1 | 1 | 1 | 1 |
| 25 | 5 | 8 | 9 | 1 | 1 | 1 | 1 | 1 | 1 |
| 26 | 4 | 7 | 9 | 1 | 1 | 1 | 1 | 1 | 1 |
| 27 | 9 | 9 | 9 | 1 | 1 | 1 | 1 | 1 | 1 |
| 28 | 6 | 8 | 9 | 1 | 1 | 2 | 1 | 1 | 1 |
| 29 | 6 | 8 | 9 | 1 | 2 | 2 | 1 | 1 | 1 |
| 30 | 4 | 6 | 9 | 1 | 1 | 1 | 1 | 1 | 1 |
| D | 9 | 9 | 9 | 2 | 6 | 6 | 1 | 4 | 4 |

-continued

| Compound No. | Dry rice | | | Digitaria | | | Setaria | | |
|---|---|---|---|---|---|---|---|---|---|
| | 0.5 | 0.25 | 0.125 | 0.5 | 0.25 | 0.125 | 0.5 | 0.25 | 0.125 |
| 1 | 9 | 9 | 9 | 9 | 9 | 9 | 9 | 9 | 9 |
| E | 3 | 6 | 9 | 2 | 2 | 3 | 1 | 2 | 4 |
| 38 | 6 | 8 | 9 | 1 | 1 | 1 | 1 | 1 | 1 |
| 39 | 6 | 9 | 9 | 1 | 1 | 1 | 1 | 1 | 2 |
| 40 | 8 | 9 | 9 | 1 | 1 | 2 | 1 | 1 | 5 |
| 41 | 6 | 8 | 9 | 1 | 1 | 2 | 1 | 1 | 1 |
| 42 | 6 | 9 | 9 | 1 | 1 | 1 | 1 | 1 | 1 |
| 51 | 5 | 8 | 9 | 1 | 1 | 1 | 1 | 1 | 1 |
| 52 | 4 | 7 | 9 | 1 | 1 | 2 | 1 | 1 | 1 |
| 53 | 5 | 7 | 9 | 1 | 1 | 2 | 1 | 1 | 1 |
| 68 | 8 | 9 | 9 | 1 | 2 | 2 | 1 | 1 | 2 |
| 69 | 9 | 9 | 9 | 1 | 1 | 2 | 1 | 1 | 2 |
| 70 | 8 | 9 | 9 | 1 | 1 | 2 | 1 | 1 | 2 |
| F | 9 | 9 | 9 | 6 | 7 | 8 | 2 | 4 | 7 |
| G | 9 | 9 | 9 | 4 | 7 | 8 | 2 | 3 | 7 |

Field experiments have also been carried out in the United States, in which three compounds according to the invention (Nos. 1, 2 and 21) were compared, in cereal crops, in respect of phytotoxicity and controlling action on Avena fatua, with the known commercial product A and with the comparison compound B, using several doses, which varied between 0.5 and 1.5 kg of active substance per hectare.

Summer barley was treated 39 days after sowing, when it was in the 4–6 leaf stage and was infested with Avena fatua in the 5–7 leaf stage, by spraying from above with the active substance dispersions.

22 days after this treatment, compound B already showed 60% damage of the barley when using 0.5 kg/ha, whilst there was only 30% damage to the barley by active substances 1, 2 and 21 according to the invention. The effect on Avena fatua was 100% in the case of all 4 active substances employed.

The active substances according to the invention are thus distinguished by substantially better selectivity when using an amount of 0.5 kg/ha, which suffices to destroy the weeds completely.

Winter wheat, which had been sown in October, was treated in March, when it had reached the 2–3 leaf stage and was infested with *Avena fatua* in the 1–5 leaf stage, by applying the aqueous active substance formulations by spraying from above.

37 days after the treatment, the comparison compound B showed 50% damage of the wheat with as little as 0.5 kg/ha, and 70% damage of the wheat with 0.75, 1 and 1.5 kg/ha, the effect on Avena fatua being 100% in each case. The comparison compound A was less phytotoxic (20% damage of the wheat at 0.5 to 1.5 kg/ha) but its effect on Avena fatua was unsatisfactory (only 30% at 0.5 kg/ha and 80% at 1.5 kg/ha).

Compounds 1, 2 and 21 according to the invention showed a substantially better overall pattern; whilst compound 1 completely destroyed the weeds at all concentrations, and caused between 20 and 50% damage to the wheat, compound 2, at 0.5 and 0.75 kg/ha, showed no damage whatsoever to the wheat, with 90% destruction of the weeds, and compound 21 also showed no damage whatsoever to the wheat at, for example, 1 kg/ha, with 100% destruction of Avena fatua.

Equally good results were achieved with summer wheat (01af). 1 month after sowing, the post-emergence spray treatment was carried out, when the wheat had formed 3 leaves and the Avena fatua 2 to 3 leaves.

15 days after application, the following pattern was found:

Comparison compound B gave 30 to 70% damage of the wheat and 60–90% destruction of the weeds at 0.5, 0.75 and 1 kg/ha; it is true that at all these concentrations compound A did not damage the wheat, but its effect on the weeds was only 30 to 50%.

In contrast, active substances 1, 2 and 21 according to the invention, when used in the above amounts of 0.5, 0.75 and 1 kg/ha, caused no damage whatsoever of the wheat and had a 70 to 90% action on the weeds.

It follows from the above that in the case of each of compounds 1, 2 and 21 according to the invention, in field tests in the abovementioned cereal crops infested with Avena fatua, it is possible to select at least one use dosage which gives optimum destruction of the weeds coupled with minimum damage to the cereal. With none of the comparison compounds in this the case; at any dose selected, these compounds are either insufficiently active against the weeds or too phytotoxic towards the cereal.

What is claimed is:

1. A compound of the formula

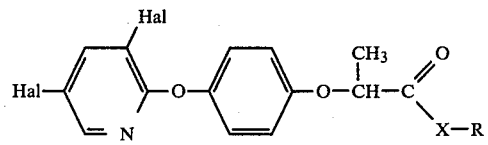

wherein each Hal is chlorine or bromine; X is oxygen or sulfur; and R is $C_1$–$C_5$ cyanoalkyl or 1-cyanocyclohexyl(1).

2. A compound according to claim 1 in which each Hal is chlorine.

3. A compound according to claim 1 in which R is $C_1$–$C_5$ cyanoalkyl.

4. The compound according to claim 2, of the formula

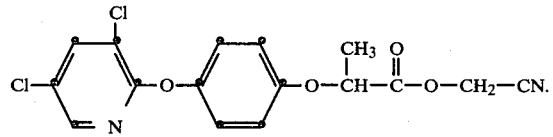

5. A herbicidal composition containing (1) a herbicidally effective amount of a compound according to claim 1 and (2) a carrier.

6. A method for selectively controlling monocotyledonous weeds in cultivated plant crops which comprises applying thereto a herbicidally effective amount of a compound according to claim 1.

* * * * *